(12) United States Patent
Epstein

(10) Patent No.: US 6,770,050 B2
(45) Date of Patent: Aug. 3, 2004

(54) MULTIPURPOSE FLUID APPLICATOR AND METHOD, WITH SURGICAL USES

(75) Inventor: Gordon Howard Epstein, Fremont, CA (US)

(73) Assignee: Baxter International Inc., Deerfield, IL (US)

( * ) Notice: Subject to any disclaimer, the term of this patent is extended or adjusted under 35 U.S.C. 154(b) by 270 days.

(21) Appl. No.: 09/819,414

(22) Filed: Mar. 27, 2001

(65) Prior Publication Data

US 2001/0011162 A1 Aug. 2, 2001

Related U.S. Application Data

(63) Continuation of application No. 09/373,489, filed on Aug. 12, 1999, now abandoned, which is a continuation of application No. 08/838,078, filed on Apr. 14, 1997, now Pat. No. 6,331,172, and a continuation of application No. 08/839,614, filed on Apr. 15, 1997, now Pat. No. 5,971,956.
(60) Provisional application No. 60/086,208, filed on May 21, 1998.

(51) Int. Cl.[7] ............................. A61M 1/00; A61M 5/00
(52) U.S. Cl. .......................................... 604/35; 604/191
(58) Field of Search ............................... 604/82, 83, 35, 604/129, 118; 239/303, 317, 549, 550, 551; 600/156

(56) References Cited

U.S. PATENT DOCUMENTS

| 2,812,765 | A | * | 11/1957 | Tofflemire | .................... 604/32 |
| 3,065,749 | A | * | 11/1962 | Heimlich | ...................... 433/88 |
| 4,299,221 | A | * | 11/1981 | Phillips et al. | ................. 604/30 |
| 5,226,877 | A | | 7/1993 | Epstein | |
| 5,585,007 | A | | 12/1996 | Antanavich et al. | |
| 5,879,340 | A | * | 3/1999 | Epstein | ........................ 604/313 |

* cited by examiner

Primary Examiner—Brian L. Casler
Assistant Examiner—Lina R. Kontos
(74) Attorney, Agent, or Firm—Jeffrey C. Nichols; Mark J. Buonaiuto; Francis C. Kowalik

(57) ABSTRACT

Multipurpose fluid applicators, particularly suitable for surgical purposes, are disclosed. The applicators are specifically designed for dispensing various combinations of sterile pressurized gas, suction, irrigation and sealant agents, including a mixed liquid sealant agent. Preferred embodiments employ a dual-acting valve selectively to control the flow of gas or suction which valve is capable of simultaneously varying flow from a source and the venting of that flow to atmosphere.

7 Claims, 12 Drawing Sheets

MULTIPURPOSE FLUID APPLICATOR AND METHOD, WITH SURGICAL USES

RELATED APPLICATIONS

This application is a continuation of commonly owned U.S. patent application Ser. No. 09/373,489 filed Aug. 12, 1999 now abandoned; which is a continuation of U.S. patent application Ser. No. 08/838,078 filed Apr. 14, 1997, now U.S. Pat. No. 6,331,772 and Ser. No. 08/839,614, filed Apr. 15, 1997 now U.S. Pat. No. 5,971,956 to patent application Ser. No. 08/946,364 filed Oct. 7, 1997 to patent application Ser. No. 09/037,160 filed Mar. 9, 1998 all naming Gordon H. Epstein as first inventor and to U.S. patent application No. 60/086,208 filed May 21, 1998 naming Mitchell E. Levinson as first inventor all of which are hereby incorporated by reference.

STATEMENT REGARDING FEDERALLY SPONSORED RESEARCH OR DEVELOPMENT (Not applicable)

BACKGROUND OF THE INVENTION

1. Field of the Invention

In particular, but not exclusively, the present invention is directed to an apparatus and process in which the following physical treatments can be applied to tissue or other work surfaces in conjunction with a clinical procedure: suction and blowing; suction, irrigation and blowing; agent application and blowing; suction, agent application and blowing; suction, sealant agent application, blowing and irrigation, to effect hemostasis, close wounds or achieve other therapeutic results. Some, or all of such combinations of treatments may be novel.

2. Description of the Related Art Including Information Disclosed under 37 CFR 1.97 and 37 CFR 1.98

Use of tissue sealants and other biological materials is an important emerging surgical technique, well adapted for the operating room or field environments such as the doctor's office or mobile medical units. In addition, the application of such sealants while performing or as necessary to perform minimimally evasive surgery reduces or eliminated the traditional problems associated with more evasive types of procedures. Preferred sealants include fibrin sealants which are formed from blood plasma components and comprise, on the one hand, a first component containing fibrinogen and Factor XIII and on the other hand a second component which usually includes thrombin, and calcium ions.

The fibrinogen is capable of a polymerizing and being cross-linked to form a solid fibrin clot when the components are mixed. The necessary additional factors to simulate relevant portions of the natural blood coagulation cascade are suitably distributed between the fibrinogen and thrombin components.

High levels of protection against transmission of infections or induction of immunological reactions can be assured by using an autologous or single-donor source for both components. Such sealants are highly effective, are biologically degraded without residue and may promote wound healing.

Depending upon the potency of the particular formulations employed, coagulation of the sealant may take place very rapidly, yielding a gel within perhaps 10 or 20 seconds after mixing of the two components.

Antanavich et al. U.S. Pat. No. 5,585,007, whose disclosure and references are hereby incorporated herein by reference thereto, provides an extensive discussion of the literature relating to fibrinogen sealant preparation (column 1, line 20 to column 4, line 62) and applicators column 4 line 62 to column 5, line 14), as well as a bibliography, (columns 6–10) and is a helpful guide to the teachings of prior workers in the field.

To foster and complement the emerging use of tissue sealants in a surgical environment there is a growing need for apparatuses and methods to assist the deployment of such materials, for example, by preparing, conditioning or manipulating the work surface or its surroundings.

As long as doctors have been performing surgery or medical procedures, inventions have been made and implemented to promote less intrusive procedures, to reduce the time required to perform procedures, and to provide enhanced patient treatments and outcomes.

It is common practice provide a surgeon at the point of care with any one or more of a number of fluids to be dispensed in or to a work surface, such as human or veterinary patient tissues, or the environment of those tissues. Some examples of such fluids are suction to remove unwanted materials and manipulate tissue and irrigation fluids such as saline.

Tofflemire U.S. Pat. No. 2,812,765 discloses a handheld applicator for selectively dispensing irrigation fluid, air, or other fluids, or suction. Tofflemire provides a frusto-conical valve B rotatable by a knob 11 to selectively connect sources of irrigation fluid I, air A or suction S with a tubular tip D. Tofflemire lacks point-of-use flow controls for any of the dispensed fluids and cannot be used for sealant dispensing, as sealant would jam valve B. Furthermore, tip D is excessively elongated, being longer than the body comprised by transverse bar 38 and sheath 43. Such elongation is unwieldy and unsuitable for dispensing a mixed sealant which might set up in the dispensing cannula, tip D.

Epstein U.S. Pat. No. 5,266,877, whose disclosure is also incorporated herein by reference, teaches one form of combination hand-held applicator which can dispense a mixed, two-component tissue sealant, discharged from on-board reservoirs, to close wounds and effect hemostasis and which is also furnished with suction means for applying suction from a cannula alongside a sealant dispensing cannula, to treat a work surface. The suction means is connectable with an external vacuum source, such as is commonly available in operating rooms.

The parent applications disclose further embodiments of multi-component, mixed sealant applicators provided with a suction-dispensing cannula, which applicators also employ dual acting suction control valves for enhanced suction control and which are able to employ suction for retrograde clearing of sealant clots from the mixed sealant pathway.

A blown air or gas stream also has utility in the surgical arena and suitable sources of pressurized gas are commonly available, flow control difficulties, the risk of air embolisms and the specialized utility of an air stream as a treatment fluid at a surgical site, raise considerable difficulties in providing applicators and methods for dispensing an air or gas stream which can safely be used in delicate surgical procedures.

For example, it may be difficult to provide a well-directed, gentle flow of air, suitable for surgical application, from the customarily available compressed air sources, and because the need for such a flow may be occasional, or low priority, it may be difficult to justify the expense and inconvenience of a suitably controlled blower as a single-purpose device.

Accordingly, there is a need for a controlled blower and blowing method suitable for applying a gas stream to a surgical site.

SUMMARY OF THE INVENTION

To solve this problem the invention provides a controlled blower and blowing method suitable for applying a gas stream to a surgical site which comprises: a blower body connectable with a pressurized gas source; a gas output cannula for directing a dimensionally controlled flow of a suitable treatment gas, for example sterilized air, to a user-selected area of the surgical site; and a user-operable control valve operable to provide a surgically desirable gas flow from the cannula.

In a preferred embodiment the control valve is a dual-acting control valve which can simultaneously enlarge a gas supply throat from the source and diminish a venting throat to provide a desired output gas flow control, particularly at low pressures and flow rates.

Preferably also the blower is a lightweight, hand-held easily manipulated device which is equipped to provide an additional or alternative fluid or fluids at the work site, for example suction, irrigation or a tissue sealant fluid. Such multiple fluid flows can be selectively dispensed by operation of a simple, manually actuated selector, switch or valve on the blower.

In one preferred embodiment, both suction and gas flow are available simultaneously, being dispensed from separate cannulas, with the gas dispensing cannula preferably having a dispensing tip retracted distally behind that of the suction cannula, whereby gas can be circulated from the gas-dispensing cannula, to the work surface and withdrawn from same by the suction cannula.

In another embodiment, suction, and gas flow are selected to be dispersed from the same cannula through a manually actuated selection valve while an irrigation fluid is available simultaneously from the other cannula.

Other embodiments are directed to: gas flow and tissue sealant being dispersed simultaneously or separately from separate cannulas; suction, tissue sealant and gas flow being dispersed simultaneously or separately from separate or several cannulas; and suction, tissue sealant, gas flow and irrigation fluids being dispersed simultaneously or separately from several cannulas.

Preferably, although not necessarily, the sealant is a biological sealant, for example a tissue adhesive, and the area of application is a biological tissue subject to surgery. The sealant components can comprise a first, structural component capable of gelling, and preferably of solidification and a second, activation component which activates such gelling and, optionally, solidification. More preferably, the sealant is a tissue sealant and the first component comprises fibrinogen and the second component comprises, or can generate a fibrinogen activator, especially thrombin or an equivalent thereof.

The invention also includes an applicator and method that provides the user with convenient and ergonomic access to an efficient means for providing suction, blowing and or irrigation in addition to or without simultaneously being able to apply mixed sealant components in accordance with the prior applications provides an novel and unique way of advancing this emerging field while also addressing traditional problems encountered in this and related fields.

The invention includes, but is not limited to, a novel surgical method of applying sealant to unexposed or internal biological surfaces, e.g. human or animal anatomical surfaces, that are accessible to a remote applicators, such as the ones disclosed in aforementioned patent applications. The use of a remote mixing chamber, which receives a flow of multiple sealant components and mixes the sealant components at the distal end of the applicator, allows the distal end of the applicator to apply a mixed sealant a work site.

In addition to the application of sealant(s), the present invention is also directed to an apparatus an method which includes manipulation of a single device to provide one or more of the following; suction, blowing and/or irrigation, in addition to, or without, simultaneously being able to apply mixed sealant components.

BRIEF DESCRIPTION OF THE DRAWINGS

One way of carrying out the invention is described in detail below with reference to the drawings which illustrate one or more specific embodiments of the invention and in which.

DESCRIPTION OF THE PREFERRED EMBODIMENTS

The present invention is directed to an applicator having among other elements, an applicator assembly which includes a combination of multiple features. One beneficial feature of the current invention is the provision of a sealant application assembly which works in cooperation with an applicator that can conveniently and selectively provide suction or one or more additional fluid outputs, for example, blowing and irrigation.

Figure 1:
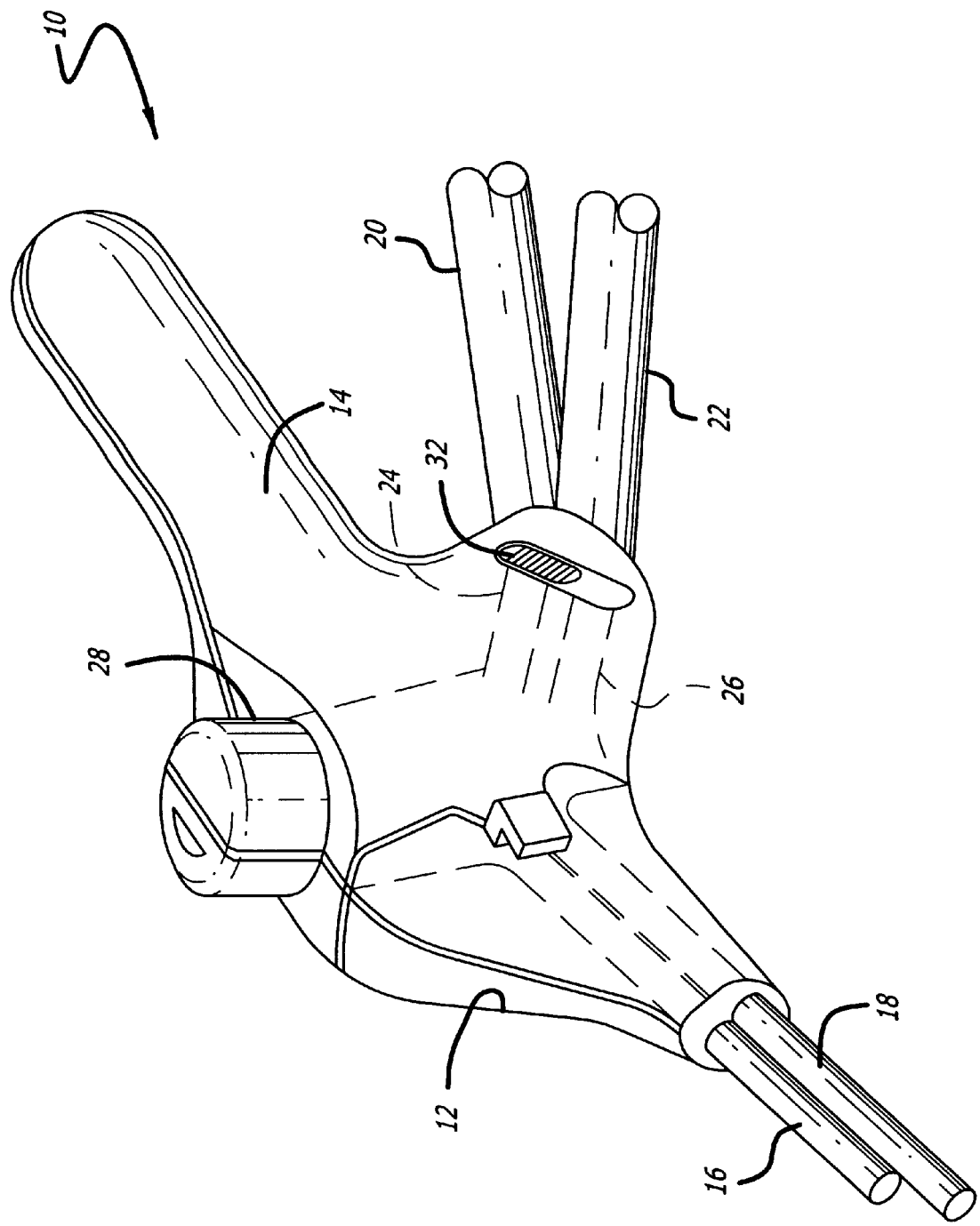
FIG. 1 is a side perspective view illustrating the first embodiment of the multi-purpose applicator according to the present invention.
Figure 2:
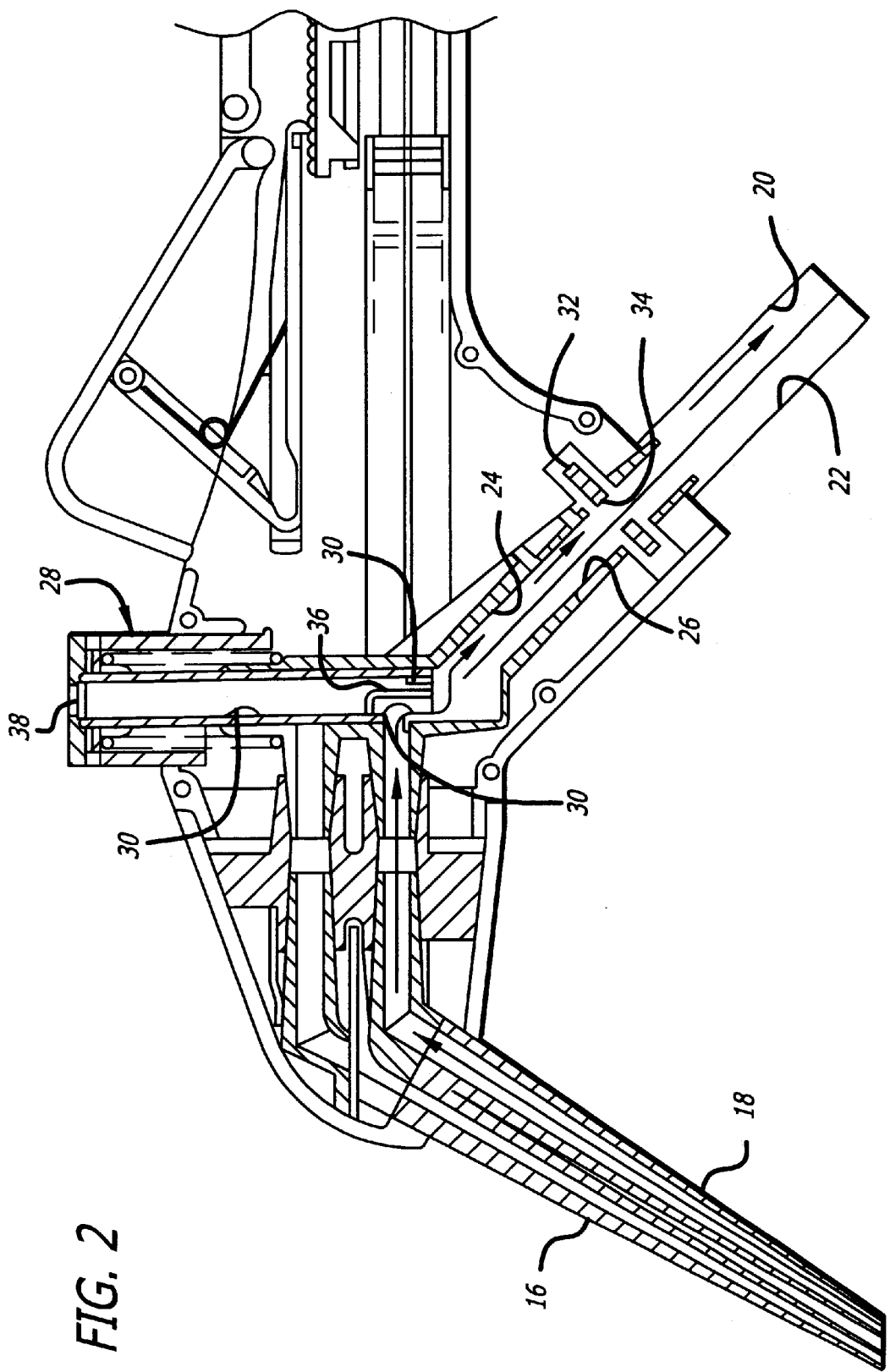
FIG. 2 is a longitudinal cross sectional view of the forward nose portion of the FIG. 1 embodiment.
Figure 3:
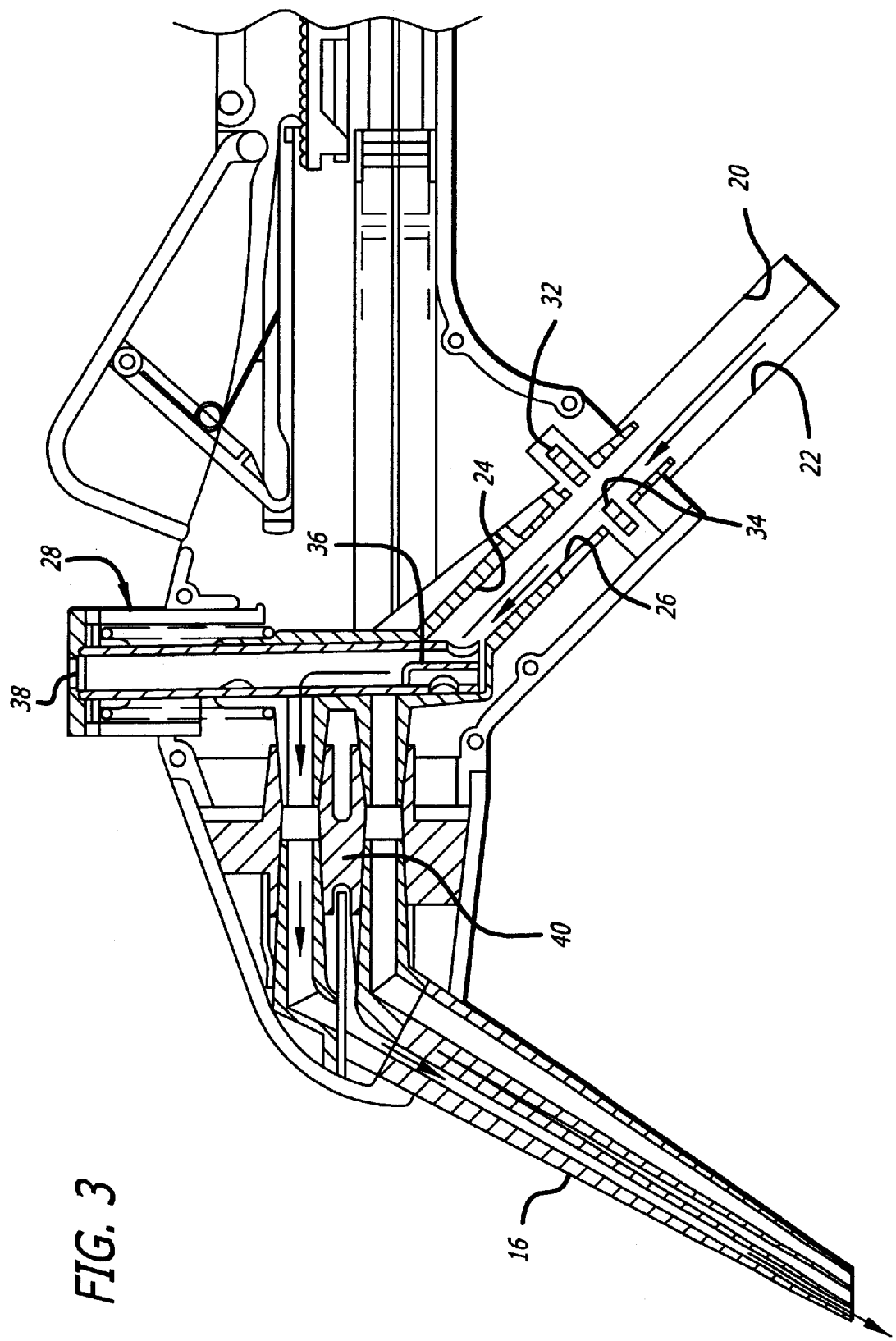
FIG. 3 is a longitudinal cross sectional view of the forward nose portion of the FIG. 1 embodiment.

Referring now to FIGS. 1–3, a first embodiment of applicator 10 of the present invention is illustrated. Applicator 10 has a nose portion 12 which communicates with a main body portion 14. Main body portion 14 supplies pressurized air and suction to nose portion 12 for use during a surgical procedure.

Suction and air are supplied to an area of application through a pair of cannulas 16 and 18, respectively.

Cannulas 16 and 18 extend outwardly from nose portion 12. A pair of supply lines 20 and 22 supply suction and compressed air to cannulas 16 and 18 through a pair of internal conduits 24 and 26.

As illustrated, cannula 18 is positioned to be further away from nose portion 12. Alternatively, cannulas 16 and 18 can be the same length. Either cannula 16 and 18 can supply suction or blowing simply by connecting the appropriate supply line.

Cannulas 16 and 18 communicate with main body portion 14, and apply suction, and compressed air to the surgical area.

A user manipulated control valve 28 allows the user to control the suction or blowing being applied by applicator 10. The gas flow being blown on the work area is useful in many ways. Blowing of the area removes liquids and debris from the area being worked. In addition, blowing may also be used to control or vary the temperature of tissue around the work area.

Control valve 28 has a plurality of valve openings 30. A selection valve 32 having an opening 34 is slidably positioned within body portion 14 to provide communication of either supply line 20 or 22 to control valve 28. Selection valve 32 is conveniently located so that it may be manipulated by the thumb of a user as he or she is gripping the device.

Moreover, the placement of selection valve 32 is such that the user's thumb can easily manipulate selection valve 32 without the user having to reposition his or her hand on applicator 10. Such ergonomic placement of selection valve 32 is particularly advantageous when applicator 10 is used in surgical applications and the surgeon or operator is relieved of having to continually attend to the instrument being used.

For instance, and as illustrated in FIG. 2, selection valve 32 is positioned to allow for communication of supply line 20 with cannula 18. Similarly, FIG. 3 illustrates communication of supply line 22 with cannula 16.

Referring now to FIGS. 2 and 3 the control of suction and blowing of applicator 10 is illustrated. Control valve 28 is similar in design to the suction control valve described in the parent patent applications except a dividing wall 36 is positioned to limit the communication of cannulas 16 and 18 with supply lines 20 and 22. (As illustrated in FIGS. 2 and 3).

Thus, as the user depresses control valve 28 to the position illustrated in FIG. 2 suction through cannula 18 is possible. The suction force can be varied by the user manipulating the position of control valve 28.

Referring now to FIG. 3, selection valve 32 is moved to seal supply line 20 and provide access to supply line 22. As control valve 28 is depressed further the suction flow through cannula 18 is cut off and pressurized air is now flowing through cannula 16.

Flow of pressurized air may be completely shut off through the use of shuttle valve 40. Shuttle valve 40 is also similar to the valve disclosed and described in the prior applications.

In addition and as discussed in the parent patent applications, control valve 28 has an opening 38 and, in addition to the repositioning of control valve 28, air flow, either suction or blowing, is further manipulated by the placement of the user's thumb over opening 38.

Figure 4:
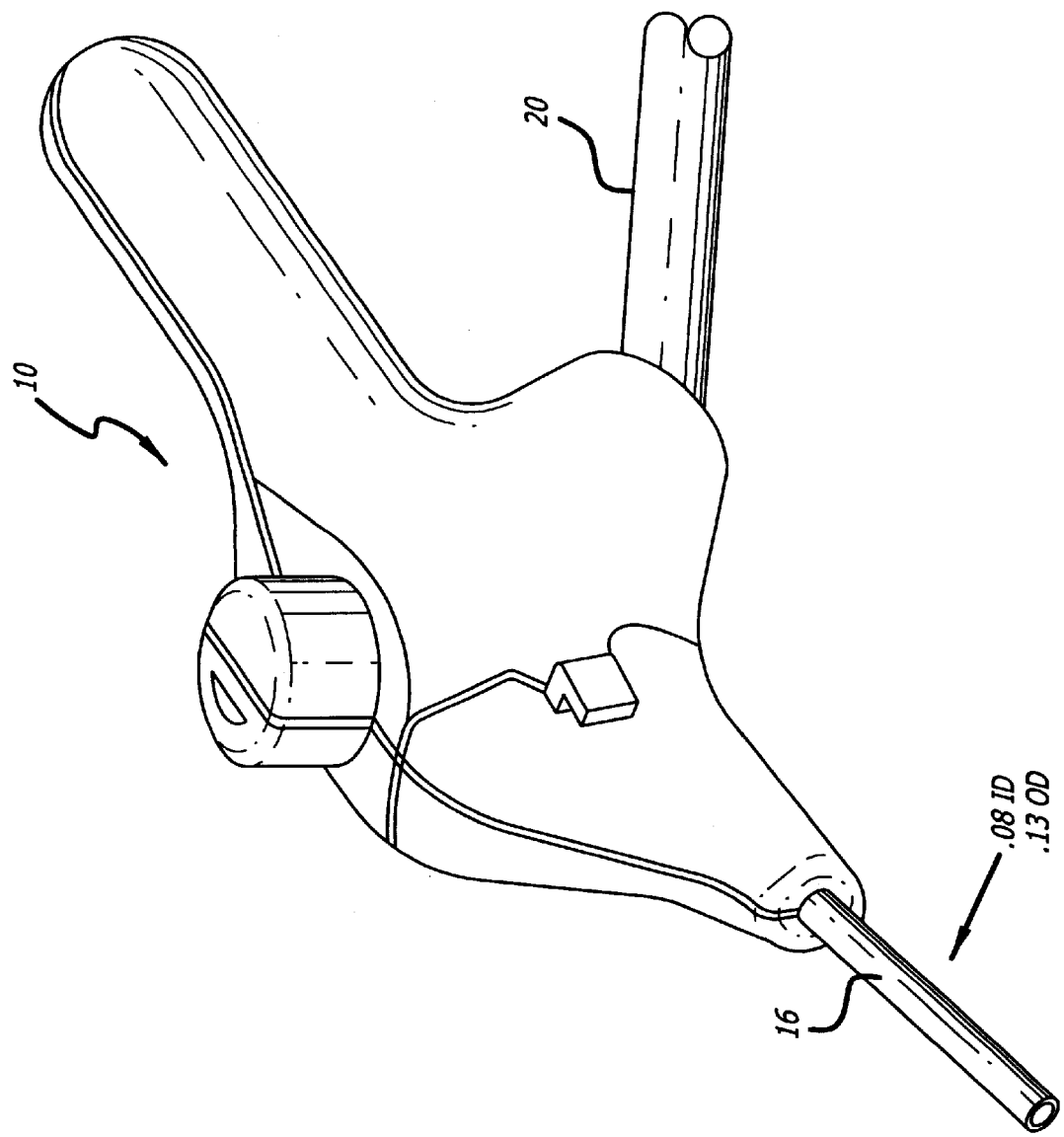
FIG. 4 is a side perspective view of an alternative to the FIG. 1 embodiment.

Alternatively and referring now to FIG. 4, applicator 10 is equipped with a single cannula 16 and a single supply line 20 which can supply suction and/or blowing to cannula 16. As required the user simply removes line 20 and replaces it with a second line that is either supplying compressed air or suction to applicator 10.

Line 20 is secured to applicator 10 with a quick release mechanism or the equivalent, such as a spring loaded casing that slides back and forth on the exterior of line 20. This allows line 20 to be quickly removed and replaced. In the preferred embodiment cannula 16 of FIG. 4 has an outside diameter of 0.13 inches and an inside diameter of 0.08 inches.

Figure 5:
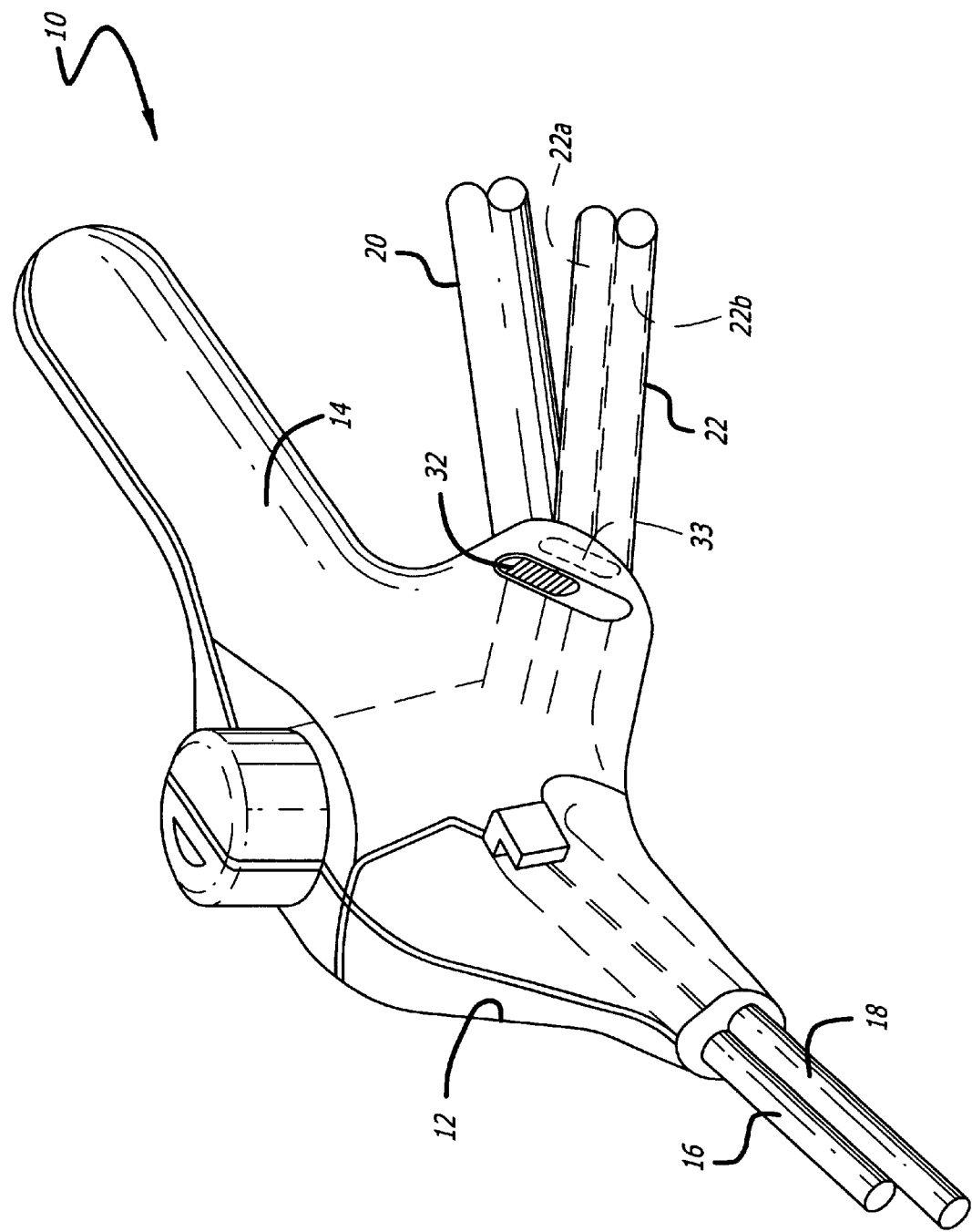
FIG. 5 is a side perspective view illustrating the second embodiment of the multi-purpose applicator according to the present invention.

Referring now to FIG. 5, the second embodiment of the present invention is illustrated. Here applicator 10 is equipped to allow a user to apply suction, irrigation and blowing to an area. In this embodiment line 20 is dedicated to supplying an irrigation fluid directly to cannula 16 while line 22 supplies suction and compressed air to cannula 18.

Irrigation fluid is a sterile saline solution, or the equivalent, for use as a means for clearing the area after suction and prior to blowing. It is also anticipated that the order of suction, blowing and irrigation may be varied as conditions so require.

As an alternative, and as illustrated by the dashed lines, line 22 may have two internal lines 22a and 22b, one supplying suction and the other compressed air. A second selection valve 33 is positioned to effect communication of lines 22a and 22b to cannula 18.

Alternatively, line 20 can also supply pressurized air to cannula 16.

Figure 6:
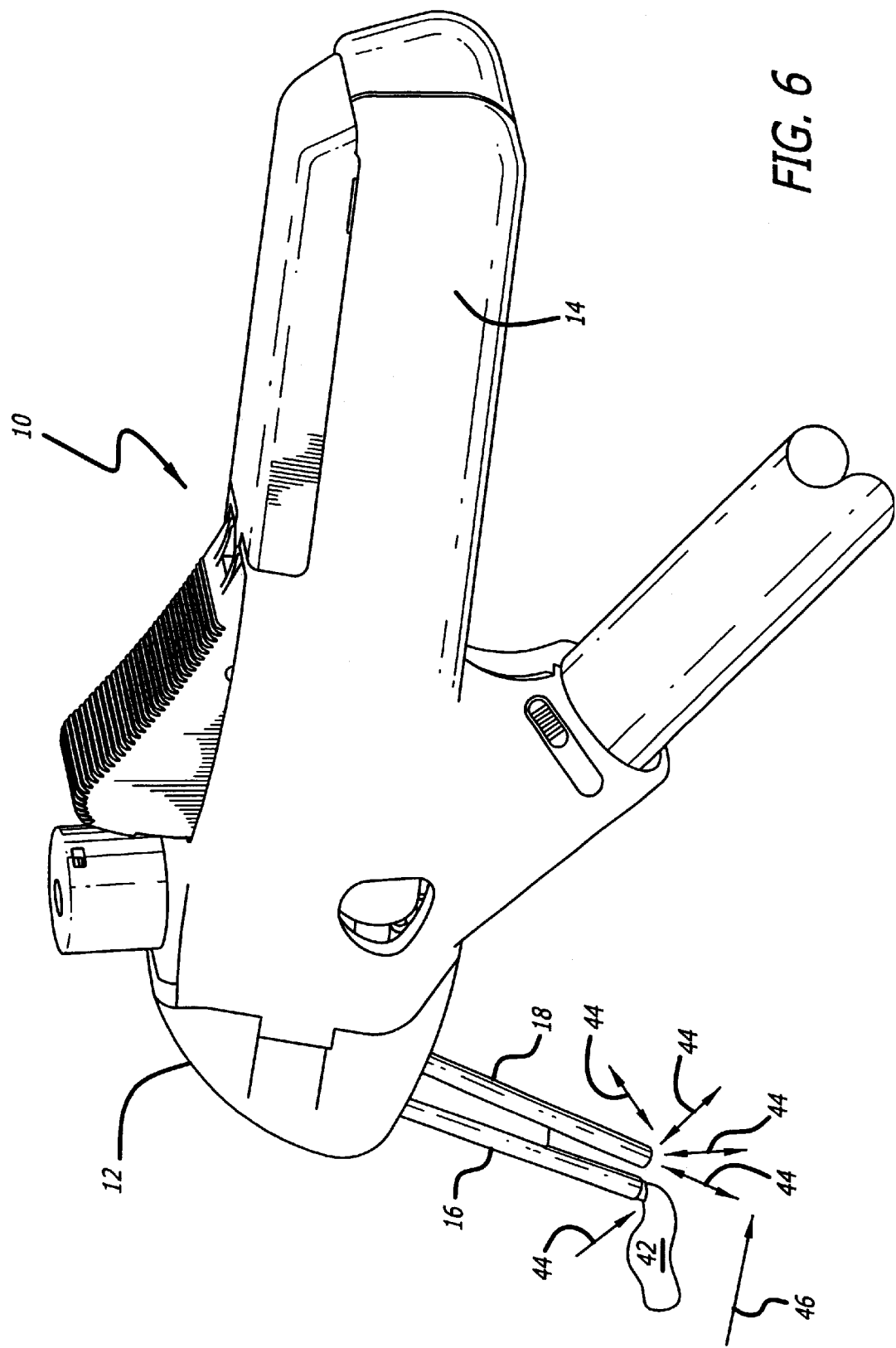
FIG. 6 is a side perspective view illustrating the third embodiment of the multi-purpose applicator according to the present invention.

Turning now to FIG. 6, a third embodiment of the present invention is illustrated. Here, cannula 16 applies a sealant 42 while cannula 18 is connected to supply line which supplies compressed air in the direction of arrows 44.

Aspects of sealant 42 application, its mixing, supply, audible indications of sealant component supply and retrograde clearing of coagulated sealant and the component parts therefor are similar to those disclosed in the parent applications. Accordingly, the detailed description of the same is incorporated herein by reference thereto.

Compressed air is blown over the area in need of surgical repair, prior to the application of sealant 42, while cannulas 16 and 18 move in the direction of arrow 46. In addition, compressed air is blown over the wound area after application of sealant 42.

Accordingly, loose debris and/or liquids such as tissue, blood, water and other types of materials, which may interfere with the adhesion of sealant 42, are blown away from the area in need of surgical repair. Blowing of the work area also dries the work area. This removal and drying can be effected prior to and after the application of sealant 42. In addition, such clearing of the work area also improves the surgeon's or operator's view of the wound area.

Figure 7:
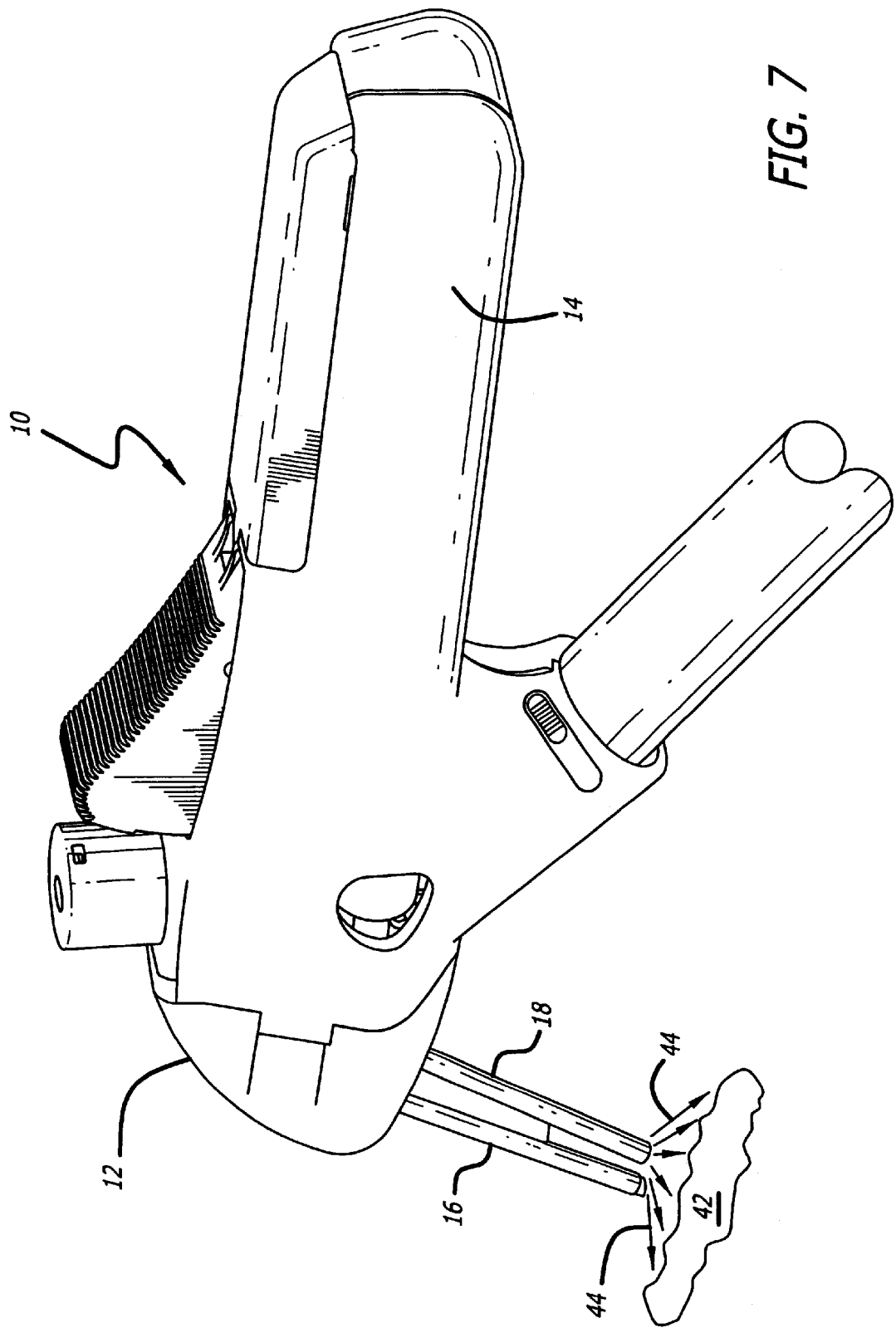
FIG. 7 is a side perspective view illustrating the third embodiment of the multi-purpose applicator according to the present invention.

Referring now to FIG. 7, applicator 10 applies a steady stream of compressed air in the direction of arrows 44. As illustrated, compressed air is being applied to recently applied sealant 42. Several passes can be made over the area until sealant 42 is cured.

The application of a controlled air stream to sealant 42 will enhance the curing time required for coagulation of sealant 42 or materials used in implants or prosthetics. In addition, the controlled air stream will also prevent debris, tissue, blood, liquids and other materials from being incorporated into curing sealant 42, reducing the risk of infection while also improving the curing of sealant 42. A controlled air stream may also be used to manipulate the temperature of the surrounding tissue. For instance, the pressurized gas being applied may be cooled or heated to provide a corresponding affect to the surrounding tissue.

In addition, several passes may also be made over the wound area before application of agent 42 to clear and dry the wound area.

A preferred compressed gas supplied to cannula 18 is a sterile carbon dioxide which because of its high diffusion coefficient dissolves rapidly and may avoid gas embolism which could occur with other gases. Also carbon dioxide is relatively inert chemically. Other sterile gases which may be used include nitrogen, air, enriched air and oxygen. Compressed gas may partially contain, gaseous or liquid medications to control infection or provide other desired therapeutic or conditioning effect. Liquids, or even finely dispersed powders, can, if desired be entrained in the gas as a suspension, for which purpose the liquids should be atomized or sprayed or otherwise distributed in space.

Figure 8:
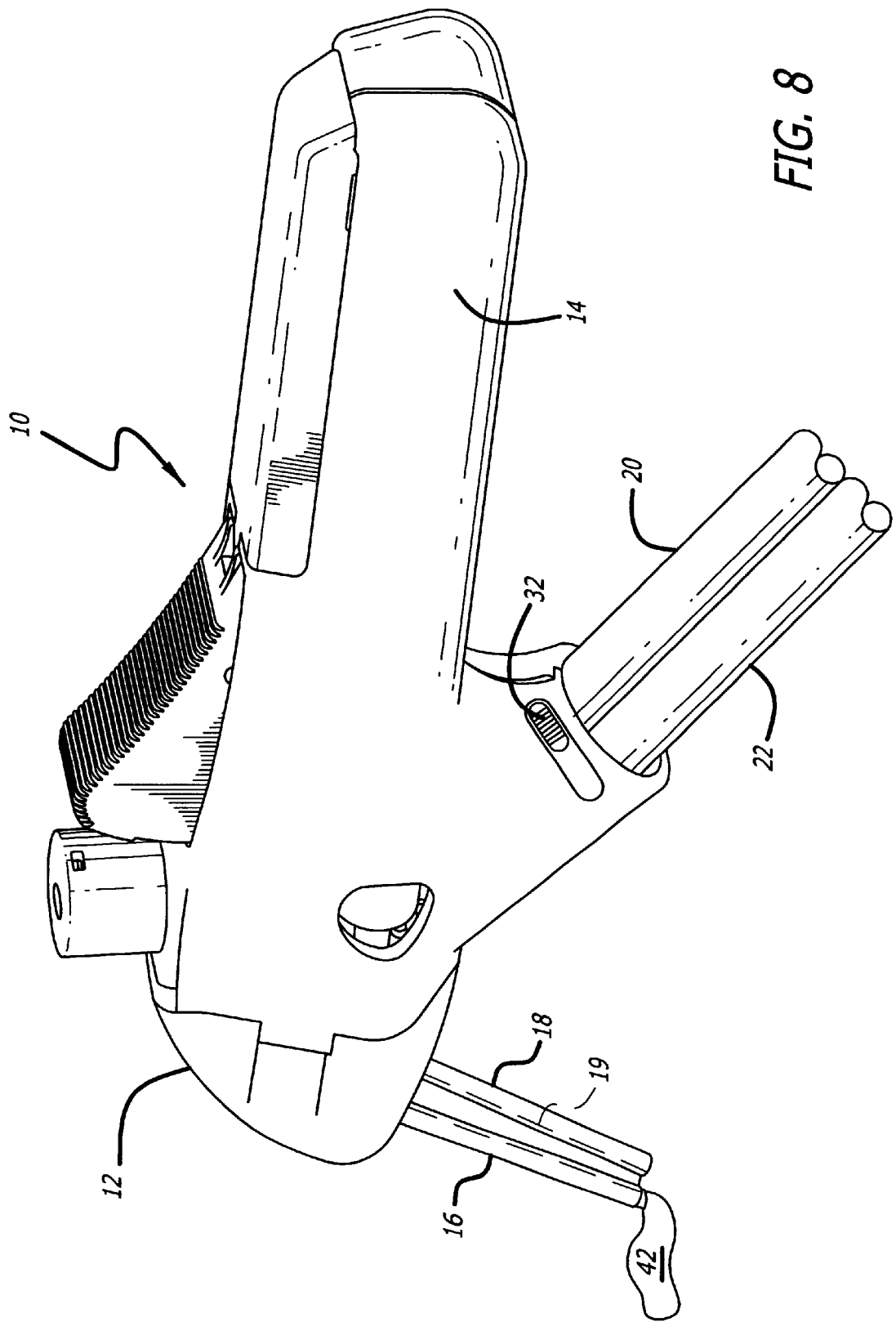
FIG. 8 is a side perspective view illustrating the fourth embodiment of the multi-purpose applicator according to the present invention.

Referring now to FIG. 8, the fourth embodiment of the present invention is illustrated. Here cannula 18 is connected to supply lines 20 and 22 each of which supplies either suction or compressed gas. Communication of cannula 18 to supply lines 20 and 22 is effectuated through selection valve 32.

Accordingly, the user can first apply suction to the wound area, apply agent 42, manipulated selection valve 32 and then apply compressed air to the applied agent. Alternatively and as the conditions of the wound area varies, the user may first apply compressed air, then apply sealant 42 and then apply suction.

As yet another alternative, and illustrated by the dashed lines, a third cannula 19 is positioned on nose potion 12. Here cannulas 18 and 19 communicate directly with supply lines 20 and 22 while cannula 16 is used for dispersment of sealant 42. Valve 32 allows the user to select either suction or blowing of compressed air. In this alternative, dividing wall 36 and openings 30 are appropriately positioned to facilitate such communication.

Figure 9:
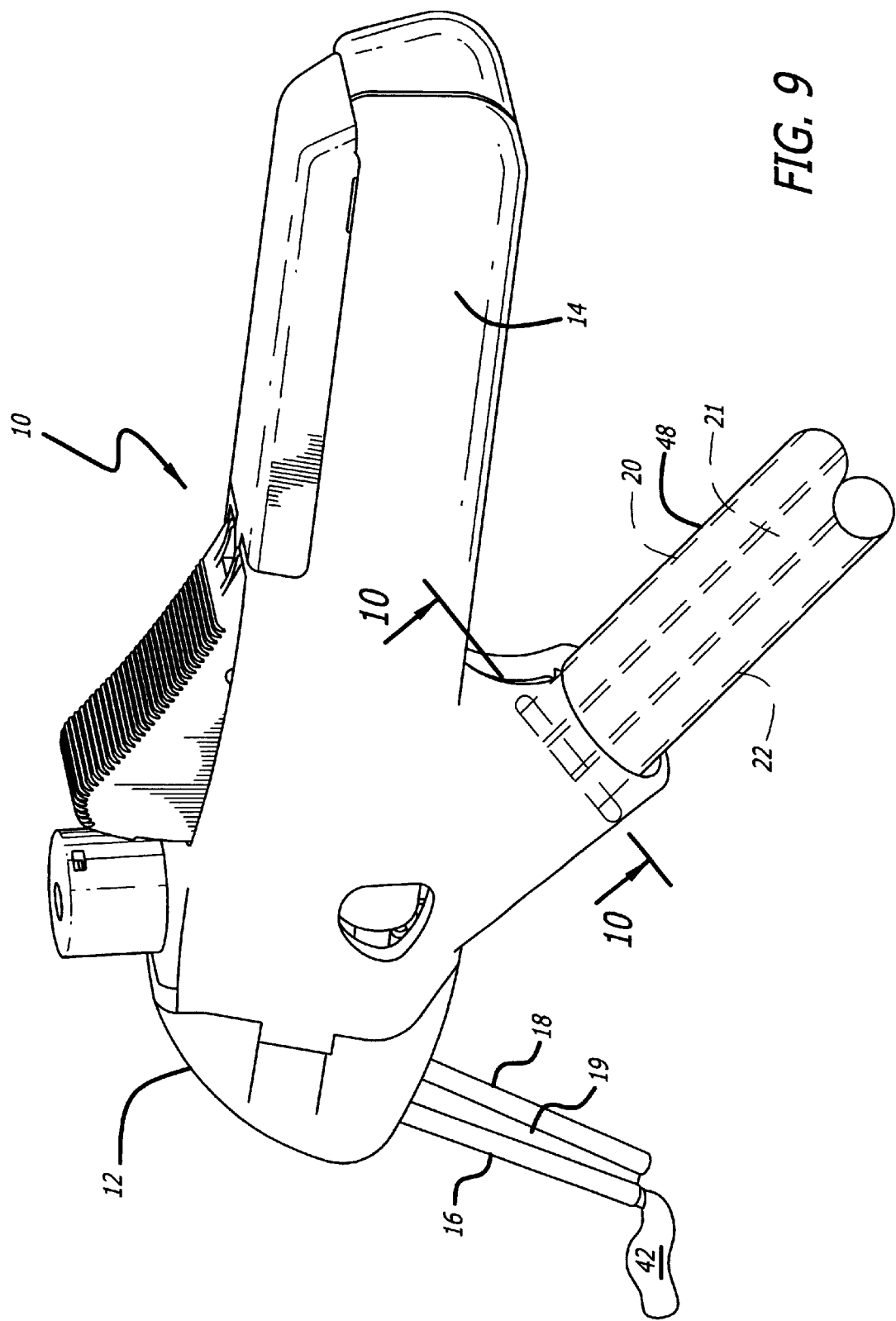
FIG. 9 is a side perspective view illustrating the fifth embodiment of the multi-purpose applicator according to the present invention.
Figure 10:
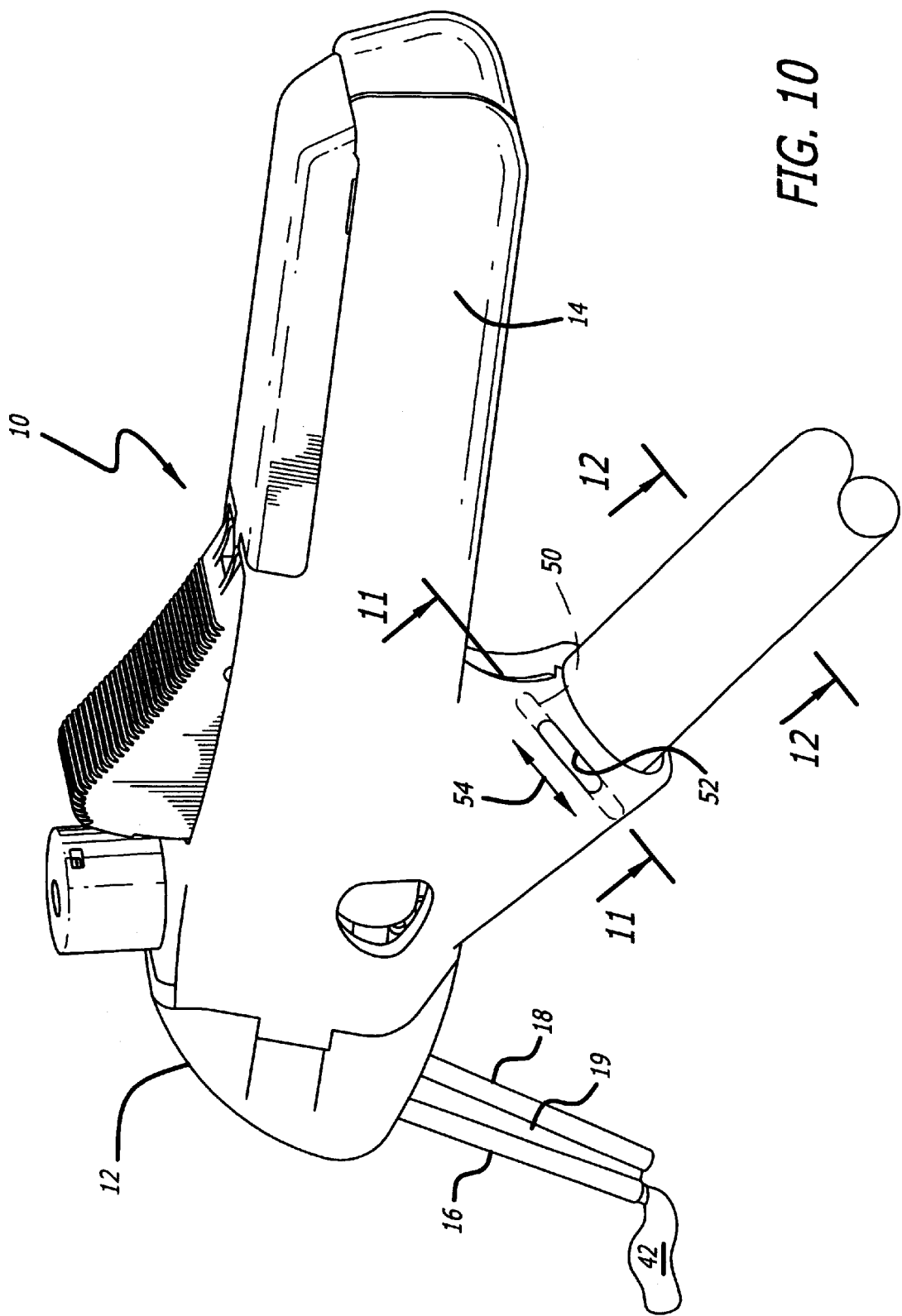
FIG. 10 is a side perspective view illustrating the fifth embodiment of the multi-purpose applicator according to the present invention.

Referring now to FIGS. 9 and 10, the fifth embodiment of the present invention is illustrated. Here cannula 16 applies agent 42, cannula 18 is connected to supply lines 20 and 22, each of which supplies either suction or compressed gas, and a cannula 19 is directly connected to a third supply line 21 which provides irrigation to cannula 19. Communication of cannulas 18 and 19 to supply lines 20–22 is effectuated through selection valve 32.

In the preferred embodiment supply lines 20, 21 and 22 are internally contained within main supply line 48. Each internal supply line is devoted to supplying either suction, compressed air or irrigation fluids to applicator 10. Cannula 18 provides either suction or blowing while cannula 19 is dedicated to supplying irrigation fluids directly supplied to cannula 19.

Accordingly, a user can first operate applicator 10 to apply suction to a wound area for removal of unwanted liquids and debris. Suction may also be used to gently grab a piece of tissue and move it to a desired location, such as in a wound closure procedure. Then sealant 42 is applied from applicator 10 to the desired location. Once sealant 42 is applied over the wound, the application device is now configured to applied compressed air over the area of application for drying and liquid and debris removal. As a final step irrigation fluid is now run through area of application.

The present invention allows a user to perform this sequence of steps without having to use multiple instruments. Additionally, the applicator 10 is constructed in accordance with the present invention to allow for such manipulation without having the user to reposition their hand.

Selection valve 32 is positioned within body portion 14 and controls the switching of supply lines 20, 21 and 22 to the appropriate cannulas. Selection valve 32 has a movable valve member in the form of a disk 50 that is manipulated by the user to select compressed air, suction or irrigation to be supplied to cannulas 18 and 19.

Disk 50 is accessible through an opening 52 in body portion 14. Opening 52 is positioned to be easily accessed by the thumb of the user as he or she is gripping the device. Disk 50 is manipulated by rotating it in the directions of arrow 54.

Moreover, the placement of disk 50 is such that the user's thumb can easily rotate disk 50 without the user having to reposition his or her hand on applicator 10. Such ergonomic placement of disk 50 is particularly advantageous when applicator 10 is used in surgical applications and the surgeon or operator is relieved of having to continually attend to the instrument being used.

Figure 11:
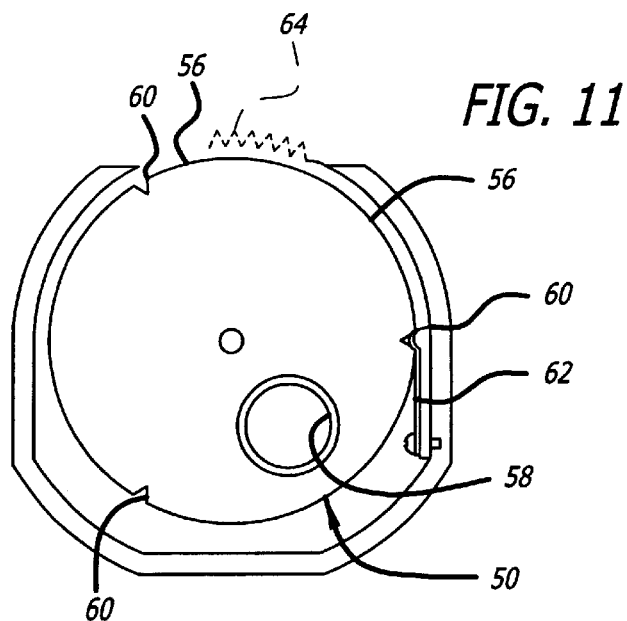
FIG. 11 is a cross sectional view along lines 11—11 of FIG. 10.
Figure 12:
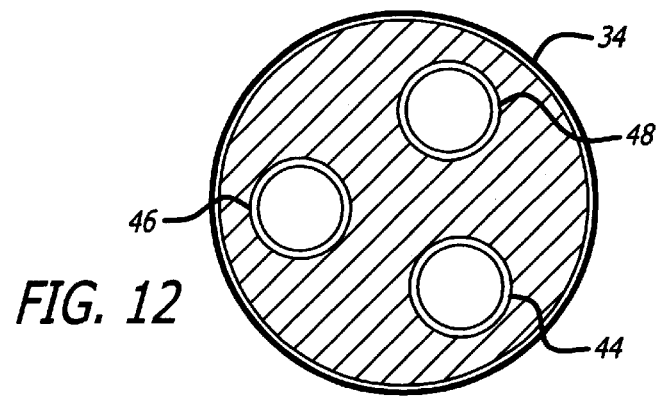
FIG. 12 is a cross sectional view along lines 12—12 of FIG. 10.

Turning now to FIGS. 11 and 12 some, but not all, possible configurations of disk 50 are illustrated. Disk 50 has an opening 58. Opening 58 is positioned to selectively provide access to one of internal supply lines 20, 21 and 22. Disk 50 has a plurality of detents 60 along the periphery 56 of disk 50 which, in cooperation with a spring 62, lock disk 50 in positions which align opening 58 with one of supply lines 20, 21 and 22.

As an alternative and to provide a more course gripping surface, an improved gripping surface 64 is incorporated into outer periphery 56 of disk 50. (see the dashed lines in FIG. 11).

As yet another alternative, periphery 56 is marked with indicia to indicate which supply line is being accessed. For instance, terms such "AIR", "SUCTION" and "IRRIGATION" may be printed along periphery 56 of disk 50 and will be visible through opening 52 to indicate the positioning of opening 58. Alternatively, or additionally, periphery 56 of disk 50 may be color coded, or it may be textured or shaped to provide a tactile indication to the user of the selected function.

Accordingly, a user can manipulate disk 50 to conveniently change the output of cannula 18.

Figure 13:
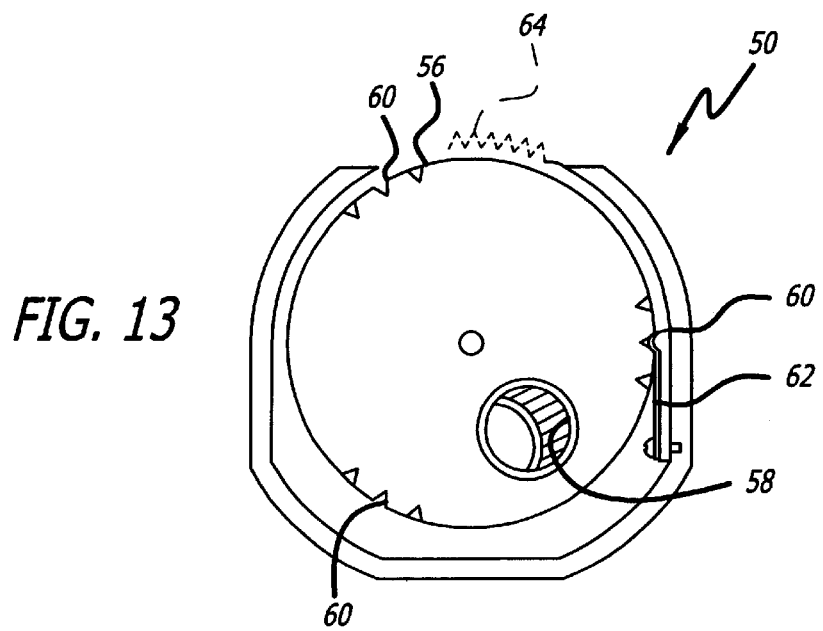
FIG. 13 is a cross sectional view of an alternative embodiment of the present.

As an alternative, detents 60 are positioned to provide locking positions in which opening 58 only partially aligns with one of the internal supply lines (FIG. 13). Such a configuration allows the user to partially access one of the internal supply lines thereby providing a reduced air or fluid flow while also manipulating the same with control valve 28.

Of course it is understood that line 48 may have more or less than three internal supply lines. Such configurations and variations may be dictated by the intended usage of applicator 10. For instance, an applicator intended primarily for suction and blowing may only require a two line configuration.

As an alternative, a single supply line 48 may be equipped with a quick release mechanism, such as spring actuated casing, or the equivalent, typically used in air supply lines. With this configuration the user simply changes the supply line as required.

Figure 14:
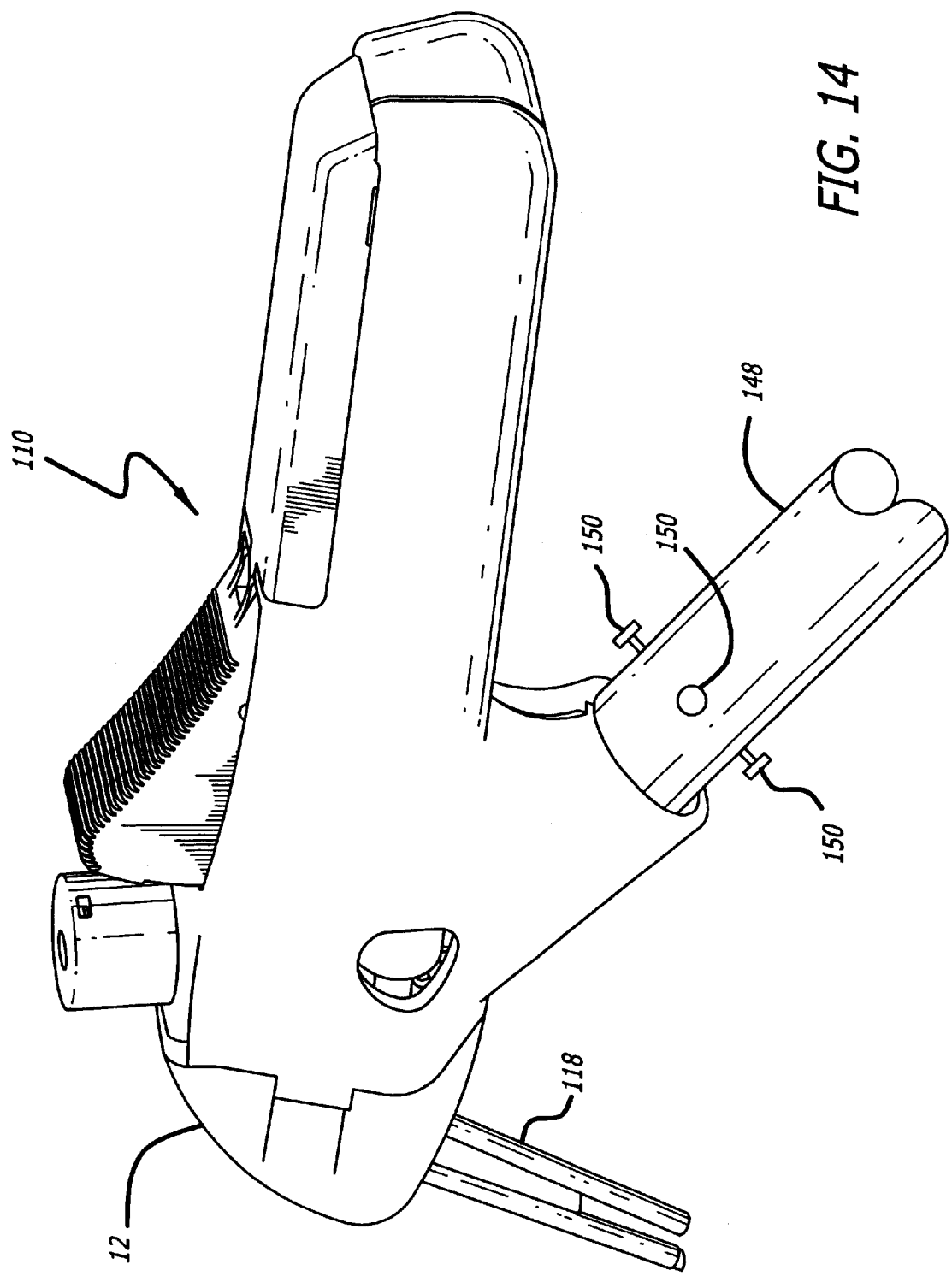
FIG. 14 is a side perspective view illustrating an alternative to FIG. 9 embodiment.

Referring now to FIG. 14 an alternative embodiment of the present invention is illustrated. Here component parts performing similar or analogous functions are numbered in multiples of 100. In this embodiment three needle valves 150 are positioned on the exterior of line 148. Valves 150 regulate the air flow and/or irrigation fluid flow of internal supply lines 120, 121 and 122 (not shown).

To adjust the output or suction to cannula 118, the user simply closes one valve and then opens another to vary the contents of cannula 118. As an alternative, the effects of valve 150 may be provided by: a clamp or roller which pinches a flexible tube; needle valves; stop-cock valves; trumpet valves; gate valves; pressure regulators; and other various flow restricting devices.

Efficiency in tissue preparation, and sealant application is particularly useful in wound closure procedures. Thus, the present invention provides a particularly advantageous method of preparing the area for sealant application.

Many of the components of the novel sealant applicators described herein can be rendered as plastics moldings from resin or polymer materials, the choice of suitable ones of which will be apparent to those skilled in the art, as will alternative materials such as metal alloys, sinters or the like. Some examples of suitable polymer materials that may be employed are: General Electric Company's ULTEM (trademark) 1000 resin; an ABS (acrylonitrile-butadiene-styrene) resin, such, for example, as Bayer AG's LUSTRAN 648 (trademark) resin; and polypropylene polymer, such for example as Montel's PRO-FAX SR-857M (trademark).

While dimensions are not critical, and embodiments too cumbersome to be dextrously manipulated by one or both hands, are contemplated, one embodiment that is particularly well suited for use by a surgeon, which is comfortable, lightweight and precisely manipulable, has an applicator body length (with tip removed) of about 15 cm (about 6 inches) and a length of reservoir within each syringe of about 5.5 cm (about 2¼ inches). With circular cylindrical reservoirs, in syringes 12, of approximately 0.9 cm (⅜ inch) diameter a reservoir capacity of about 3 cc, each, total 6 cc with two reservoirs, is provided. A preferred length for cannulas 16, 18 and 118 when embodied in an applicator of such proportions is less than about 5 cm. (2 in.) and more preferably in the range of about 1–3 cm. (about 0.4–1.2 in.), providing an ergonomic, easily manipulated applicator. Thus, cannulas 16, 18 and 118 are preferably much shorter than the body of the applicator, and the distance any mixed sealant travels (if such is employed) from the point of mixing is relatively short, preferably not more than about 5 cm or more preferably no more than about 3 cm. Such dimensions as these provide an applicator which is comfortable and ergonomic for most surgeons to use with precision. Preferred constructions may vary these dimensions by up to about 10, or less preferably 20 percent. Less demanding applications may vary the given or corresponding dimensions by up to about 50 percent while still providing an applicator that can be supported and comfortably manipulated in one hand.

Employing the applicators and methods of the invention, blowing of a sterile and preferably inert gas can be used for clearing away of fluids such as blood during surgery to enhance visibility and access to the surgical site. When applying surgical agents, such as fibrin sealant, it is useful to clear the substrate of fluid and debris before application of the agent. Blowing of a sterile gas can be used for this purpose, either with constant or variably controlled flow. Drying of a surface is also important to promote adhesion or hemostasis prior to application of a sealant. Drying can be attained using blowing. Delivery of gaseous surgical agents or liquid agents which can be suspended in a gas can be facilitated by a blowing device.

While illustrative embodiments of the invention have been described, it is, of course, understood that various modifications will be apparent to those of ordinary skill in the art. Such modifications are contemplated as being within the spirit and scope of the present invention which is limited and defined only by the appended claims.

What is claimed is:

1. A handheld multipurpose tissue sealant applicator comprising:
   a hand-grippable body;
   a first cannula through which a fluid can be dispensed extending from the hand-grippable body and configured to dispense a tissue sealant;
   a second cannula extending from the hand-grippable body adjacent the first cannula;
   a vacuum supply line connected to a vacuum source, said vacuum supply line in fluid communication with the second cannula;
   a pressurized gas supply line connected to a source of pressurized gas, said pressurized gas supply line in fluid communication with the second cannula; and
   a manually operable control valve system selectively controlling communication between the second cannula and each of the vacuum supply line and the pressurized gas supply line.

2. The applicator according to claim 1 further comprising a common pathway communicating with the pressurized gas supply line and the vacuum supply line and wherein said valve system comprises:
   a first control valve controlling communication between the first common pathway and either the pressurized gas supply line and the vacuum supply line; and
   a second control valve controlling communication between the common pathway and the second cannula.

3. The applicator according to claim 2 wherein said first control valve comprises a first control valve selector switch.

4. The applicator according to claim 1 further comprising an irrigation fluid source in fluid communication a third cannula disposed adjacent the first and second cannulas.

5. The applicator of claim 1 wherein said tissue sealant comprises a fibrin tissue sealant.

6. A handheld multipurpose tissue sealant applicator, comprising:
   a hand-grippable body;
   a first cannula through which a fluid can be dispensed from the applicator configured to dispense a tissue sealant and extending from the hand-grippable body;
   a second cannula extending from the hand-grippable body adjacent the first cannula;
   a third cannula extending from the hand-grippable body adjacent the first and second cannulas;
   an irrigation fluid supply line connected to a source pressurized irrigation fluid and in fluid communication with the second cannula;
   a vacuum supply line in fluid communication between and with a vacuum source, and the third cannula;
   a pressurized gas supply line in fluid communication between and with a source of pressurized gas and the third cannula; and
   a valve system comprising a first control valve controlling communication between the third cannula and either the vacuum supply line and the pressurized gas supply line fluid pathway.

7. A method of applying a tissue sealant to a work surface, comprising:

providing a hand held multipurpose applicator in communication with a pressurized source of tissue sealant, a vacuum source, and a pressurized gas source;

selectively controlling communication between said applicator and either said source of pressurized gas or said vacuum source; and selectively controlling communication between said applicator and said pressurized source of tissue sealant.

* * * * *